(12) United States Patent
Kang et al.

(10) Patent No.: US 8,993,291 B2
(45) Date of Patent: Mar. 31, 2015

(54) THERMOCOCCUS MUTANT HAVING IMPROVED HYDROGEN PRODUCTION FROM FORMATE AND METHODS OF HYDROGEN PRODUCTION BY USING THEREOF

(71) Applicant: Korea Institute of Ocean Science & Technology, Gyeonggi-Do (KR)

(72) Inventors: Sung Gyun Kang, Gyeonggi-do (KR); Jung Hyun Lee, Gyeonggi-do (KR); Kae Kyoung Kwon, Gyeonggi-do (KR); Hyun Sook Lee, Gyeonggi-do (KR); Tae Wan Kim, Gyeonggi-do (KR); Yun Jae Kim, Gyeonggi-do (KR); Min Sik Kim, Gyeonggi-do (KR); Jeong Ho Jeon, Incheon (KR)

(73) Assignee: Korea Institute of Ocean Science & Technology, Gyeonggi-Do (KR)

( * ) Notice: Subject to any disclaimer, the term of this patent is extended or adjusted under 35 U.S.C. 154(b) by 0 days.

(21) Appl. No.: 14/251,713

(22) Filed: Apr. 14, 2014

(65) Prior Publication Data
US 2014/0295519 A1 Oct. 2, 2014

(30) Foreign Application Priority Data

Mar. 28, 2013 (KR) .......................... 10-2013-0033345

(51) Int. Cl.
*C12P 3/00* (2006.01)
(52) U.S. Cl.
CPC ....................................... *C12P 3/00* (2013.01)
USPC .......................................................... 435/168

(58) Field of Classification Search
USPC .......................................................... 435/168
See application file for complete search history.

(56) References Cited

FOREIGN PATENT DOCUMENTS

| KR | 10-0315662 B1 | 11/2001 |
| KR | 10-0315663 B1 | 11/2001 |
| KR | 10-2011-0069744 A | 6/2011 |
| KR | 10-2012-0103238 A | 9/2012 |

OTHER PUBLICATIONS

Moon et al., "Proteome Analyses of Hydrogen-producing Hyperthermophilic Archaeon *Thermococcus* onnurineus NA1 in Different One-carbon Substrate Culture Conditions", Molecular & Cellular Proteomics, (11):6M111.015420. DOI: 10.1074.mcp.M111.015420.*
Kim et al., "Formate-driven growth coupled with H2 production", Nature, Sep. 2010, 467:352-356. DOI:10.1038/nature09375.*
Bae et al., "H2 production from CO, formate or starch using the hyperthermophilic archaeon, *Thermococcus* onnurineus", Biotechnol Lett (2012) 34:75-79. DOI: 10.1007/s10529-011-0732-3.*

* cited by examiner

Primary Examiner — Suzanne M Noakes
(74) Attorney, Agent, or Firm — The PL Law Group, PLLC

(57) ABSTRACT

The present invention relates to a *Thermococcus onnurineus* NA1 mutant having an increased ability to produce hydrogen from formate and a method of producing hydrogen the same. The *Thermococcus onnurineus* NA1 mutant according to the invention has an increased ability to produce hydrogen in a formate-containing medium compared to wild-type *Thermococcus onnurineus* NA1 and shows an increase in growth rate compared to the wild-type. The use of the mutant strain according to the invention can produce hydrogen with high efficiency from formate.

9 Claims, 4 Drawing Sheets

THERMOCOCCUS MUTANT HAVING IMPROVED HYDROGEN PRODUCTION FROM FORMATE AND METHODS OF HYDROGEN PRODUCTION BY USING THEREOF

BACKGROUND

1. Field of the Invention

The present invention relates to a *Thermococcus* mutant having an increased ability to produce hydrogen from formate and a method of producing hydrogen using the same.

2. Description of the Prior Art

The use of hydrogen in industrial areas has increased each year, and the use of hydrogen as a clean energy source for fuel cell vehicles and hydrogen power plants has gradually increased. Thus, it is expected that the supply of hydrogen will increase by geometric progression. As the value of hydrogen as clean energy increases and a method capable of steadily supplying a large amount of hydrogen is receiving attention, studies on methods for producing hydrogen have been actively conducted.

Hydrogen energy has an energy density that is three times higher than that of petroleum while it does not emit environmentally harmful materials such as carbon dioxide, NOx and SOx, and thus it receives attention as energy that will substitute for fossil fuels.

Conventional method for producing hydrogen include the electrolysis of water, the thermal-cracking or steam reforming of natural gas or naphtha, etc. However, such methods have problems in that it is required to form the conditions of high-temperature and high-pressure using fossil fuels and in that a gas mixture containing carbon monoxide is generated and it is difficult to remove carbon monoxide from this gas mixture.

On the other hand, biological methods of producing hydrogen using microorganisms have advantages in that it is not required to form the conditions of high-temperature and high-pressure by the use of energy and in that the gas produced contains no carbon monoxide. Such biological methods for producing hydrogen can be largely divided into methods based on the use of photosynthetic microorganisms and methods based on the use of non-photosynthetic microorganisms (mainly anaerobic microorganisms). Examples of the former include Korean Patent Registration No. 10-0680624, entitled "Method of producing hydrogen using the photosynthetic bacterial strain *Rhodobacter sphaeroides* having an excellent ability to produce hydrogen at high salt concentration".

However, the development of technology for high-concentration culture of photosynthetic bacteria that use light as an energy source is not yet sufficient, and conventional photosynthetic bacteria severely inhibit a substrate under high partial pressure. In addition, there is a disadvantage in that these photosynthetic bacteria can show the ability to produce hydrogen even in the presence of light.

Thus, there have been continued attempts to hydrogen using microorganisms capable of hydrogen using organic carbon compounds. Examples of such attempts include Korean Patent Registration No. 10-0315663, entitled "*Citrobacter* sp. strain Y19 and production of hydrogen thereby", and Korean Patent Registration No. 10-0315662, entitled "*Rhodopseudomonas palustris* P4 and production of hydrogen thereby".

Korean Patent Publication No. 10-2011-0069744 discloses a FDH2-MFH2-MNH2 hydrogenase cluster and describes that fdh2-mfh2-mnh2 is important in producing hydrogen from formic acid.

Korean Patent Publication No. 10-2012-0103238 filed in the present inventors discloses a method of producing hydrogen using a *Thermococcus* sp. strain.

However, the role of F420-reducing hydrogenase in producing hydrogen from formic acid has not yet been reported. The present inventors increased the expression of F420-reducing hydrogenase (frh) in a *Thermococcus* sp. strain, based on the fact that F420-reducing hydrogenase (frh) is present immediately before the fdh2-mfh2-mnh2 cluster that produces hydrogen from formic acid, and as a result, the present inventors found that the production of hydrogen in the *Thermococcus* sp. strain was increased, thereby completing the present invention.

SUMMARY

It is an object of the present invention to provide a strain having an increased ability to produce hydrogen.

Another object of the present invention is to provide a method of efficiently producing hydrogen using the strain.

Other objects and advantages of the present invention will be more clearly understood from the following detailed description of the invention, the appended claims and the accompanying drawings.

To achieve the above objects, in a first aspect, the present invention provides a mutant strain of *Thermococcus* spp., which comprises overexpressed F420-reducing hydrogenase and has an increased ability to produce hydrogen. Herein, the *Thermococcus* spp. is *Thermococcus onnurineus*, and more preferably a microorganism deposited under the accession number KCTC 12356BP, but is not limited thereto.

In a second aspect, the present invention provides a method for producing hydrogen, comprising the steps of: mutating *Thermococcus* spp. to increase the expression of F420-reducing hydrogenase therein; and culturing the mutated *Thermococcus* spp. in a medium containing formate. Herein, the *Thermococcus* spp. is *Thermococcus onnurineus*, and more preferably a microorganism deposited under the accession number KCTC 12356BP, but is not limited thereto.

The increase in the expression of the F420-reducing hydrogenase may correspond to an increase in the copy number of the F420-reducing hydrogenase gene, an increase in the translation of the gene, an increase in the transcription of the gene, an increase in the stability of the F420-reducing hydrogenase, or a combination thereof. An increase in the copy number of the gene, an increase in the translation of the gene, or an increase in the stability of the enzyme can be achieved using any conventional technique known in the art. As used herein, the term "expression" refers to the transcription and translation of a gene sequence leading the generation of the corresponding protein product of the gene. In a preferred aspect of the present invention, the gene encoding F420-reducing hydrogenase is overexpressed into the microorganism. The terms "increased expression", "enhanced expression" or "overexpression" are used interchangeably in this specification and have similar meaning, i.e. that the transcription and translation of the gene is increased compared to a non-recombinant microorgansim, leading to an increased amount of enzyme into the cell.

To increase the expression of the gene, those skilled in the art know different ways to manipulate genes expression. In particular, the gene may be expressed using inducible promoters having different strengths. These promoters may be homologous or heterologous. A person man skilled in the art knows which promoters are the most convenient. For example, glutamate dehydrogenase promoter (Pgdh), promoters Ptrc, Ptac, Plac or the lambda promoter cI are widely used.

In an embodiment of the invention, the gene may be expressed by a plasmid or vector introduced into the microorganism. The microorganism is then said a "host microorganism", referring to a microorganism able to receive foreign or heterologous genes or extra copies of its own genes and able to express those genes to produce an active protein product.

The term "transformation" refers to the introduction of new genes or extra copies of existing genes into a host organism.

The term "transformation vector" refers to any vehicle used to introduce a polynucleotide in a host organism. Such vehicle can be, for example, a plasmid, a phage or other elements known from those skilled in the art according to the organism used. The transformation vector may usually contain, in addition to the polynucleotide or the expression cassette, other elements to facilitate the transformation of a particular host cell. An expression vector comprises an expression cassette allowing the suitable expression of the gene borne by the cassette, and additional elements allowing the replication of the vector into the host organism. An expression vector can be present at a single copy in the host organism or at multiple copies. Those skilled in the art know different types of plasmids that differ with respect to their origin of replication and thus their copy number in the cell.

Another mean to obtain an overexpression of the genes is to modify the expression or regulation of the elements stabilizing the corresponding messenger RNA (Carrier et al. Biotechnol Bioeng. 59:666-72, 1998) if translation of the mRNA is optimized, then the amount of available enzyme is increased.

DETAILED DESCRIPTION

Figure 1A:
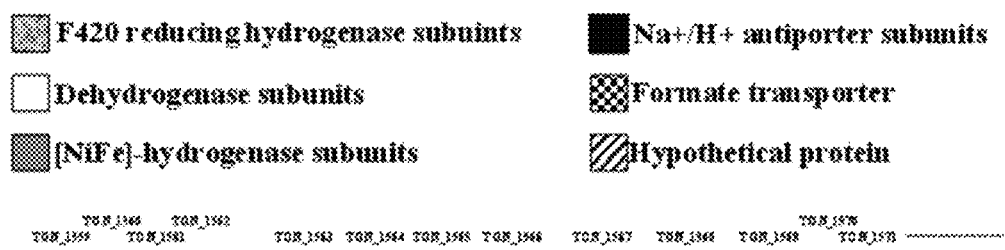
FIG. 1A shows the results of analyzing the genetic structure of the frh-fdh2-mfh2-mnh2 cluster of *Thermococcus onnurineus* NA1.

Hereinafter, the present invention will be described in further detail with reference to examples. It is to be understood, however, that these examples are for illustrative purposes only and are not intended to limit the scope of the present invention.

EXAMPLES

Experimental Method and Materials

1) Strain and Medium
Under general culture conditions, modified-MI medium (containing yeast extract (4 g/l), NaCl (35 g/l), KCl (0.7 g/l), $MgSO_4$ (3.9 g/l), $CaCl_2.H_2O$ (0.4 g/l), $NH_4Cl$ (0.3 g/l), $Na_2HPO_4$ (0.15 g/l), $NaSiO_3$ (0.03 g/l), $NaHCO_3$ (0.5 g/l), and cysteine.HCl (0.5 g/l)) supplemented with 400 mM sodium formate was used in an anaerobic environment at 80° C. After sterilization, 1.0 ml of a trace element mixture, 1 ml/l of Fe-EDTA and 1 ml/l of Balch's vitamin solution were added to the medium. The initial pH of the medium was adjusted to 6.5 at atmospheric pressure.

2) Cell growth and construction of Mutant Strain
An anaerobic chamber (Coy Laboratory Products, Inc.) was used for cell inoculation. Cells were grown in MM1-sodium formate medium at 80° C. Cell growth was monitored by measuring the amount of protein in 1 ml of the cell culture based on the optical density (OD600) at 600 nm during culture using a UV-vis spectrophotometer (Biophotometer plus, Eppendorf) or a DC protein assay kit (DCW) based on the assumption that the amount of cellular protein is approximately 50% of dry cell weight (DCW) (Kengen & Stams, 1994). One unit of OD600 corresponds to 0.361 g-DCW/L. Transformation and disruption were performed according to *Thermococcus kodakarensis* (Matsumi et al., 2007). Briefly, an about 1-kb DNA region having the target gene linked thereto was inserted into both sides of a $P_{gdh}hmg_{Pfu}$ cassette cloned into a pUC118 vector. Cells cultured in ASW-YT medium were transformed with the resulting vectors (2-6 µg) and incubated using Simvastatin as a selection marker. A mutant candidate was confirmed by PCR amplification.

The developed microorganism, *Thermococcus onnurineus* NA1, was duly deposited with Korean Collection for Type Cultures (KCTC) (having the address of Biological Resource Center (BRC), Korea Research Institute of Bioscience and Biotechnology (KRIBB), 52 Eoeun-dong, Yuseong-gu, Daejeon 305-333, Republic of Korea) under the Access number of KCTC 12356BP on Jan. 23, 2013. The deposit has been made under the terms of the Budapest Treaty and all restrictions imposed by the depositor on the availability to the public of the biological material will be irrevocably removed upon the granting of a patent.

3) Analysis of Gas
The analysis of gas composition was performed using an YL6100 gas chromatograph (GC) (YL Instrument Co.) equipped with a Molsieve 5A column (Supelco, Bellefonte, Pa.), a Porapak N column (Supelco), a thermal conductivity detector, and a flame ionization detector. Argon was used as a carrier gas. To quantify hydrogen gas, a gas calibration standard (Supleco) containing 1% (w/w) of each of components (CO, $CO_2$, $H_2$, $CH_4$ and $O_2$) in nitrogen was used.

4) Western Blotting
An antibody was obtained from a protein (frh a subunit) over-expressed in *E. coli* BL21 and purified by a Ni-NTA column. The cells grown exponentially in MM1-formate were collected by centrifugation and disrupted by sonication. The cell debris was removed by centrifugation, and the protein concentration of the crude extract was quantified using Bio-Rad protein assay solution. 5 µg of the crude extract of each strain was resuspended in 10% SDS-PAGE and transferred to a PVDF membrane with Trans-BlotTurbo™ transfer pak. The membrane was immersed in Tris-buffered saline containing 0.1% TritonX-100 (TBST) supplemented with 0.5% BSA. Antibody diluted at 1:5000 was added to the membrane and then incubated in TBS-T buffer. Horse raddish peroxidase-conjugated anti-rabbit antibody (Ab Frontier) was used as secondary antibody, and the signal generated by Immun-Star™ HRP chemifluorescence kit (Bio-Rad) was observed by ChemiDoc™ MP imaging system (Bio-Rad).

5) Kinetic Analysis of Production of Hydrogen in Wild-Type Strain and Mutant Strain Kinetic analysis for hydrogen production was performed in a continuous stirred tank reactor (CSTR) having a 2-liter working volume and a 3-liter sparger (5-diameter hole size) at 80° C. in an anaerobic mode. Agitation speed was 150 rpm, and pH was adjusted to 6.2±0.1 using 4M formic acid containing 3.5% NaCl. Seed culture was performed at 80° C. until the exponential growth phase was reached. 5 ml of the seed culture was inoculated into the CSTR by a 10-ml syringe. MM1-medium containing 400 mM sodium formate was used. Hydrogen gas was measured using the gas chromatograph YL6000 GC instrument equipped with a Molesieve 5A column (Supelco, Bellefont, Pa.), a Porapak N column (Supelco) and a TCD detector. Argon was used as a gas carrier. The oven temperature was 40° C. 10 µl of a gas sample for analysis was taken with a gas-tight syringe through the butyl rubber plug of the culture bottle. The measurement of the detected hydrogen gas was calculated by comparing the peak area with a calibration curve obtained by regression analysis using a standard gas containing 40% hydrogen in nitrogen.

Example 1

Increase in Expression of F420-Reducing Hydrogenase in *Thermococcus onnurineus* NA1

The ratio of hydrogenase and related proteins in the genome of *T. onnurineus* NA1 was found to be high (5.5%), reflecting enhanced conservation or recycling of reducing potentials in association with oxidoreductases, including CO dehydrogenase and formate dehydrogenases. According to the hydrogenase classification system of Vignais et al., the F420-reducing hydrogenase (frh) in *T. onnurineus* NA1 belongs to group 3 (Silva, P. J., van den Ban, E. C., Wassink, H., Haaker, H., de Castro, B., Robb, F. T. and Hagen, W. R. (2000) Enzymes of hydrogen metabolism in *Pyrococcus furiosus*. Eur. J. Biochem. 267, 6541-6551).

As shown in FIG. 1A, F420-reducing hydrogenase (TON_1559-1561) comprising α/β/γ subunits is located before fdh2-mfh2-mnh2 to make one cluster. The subunits of F420 hydrogenase had unique primary sequences, showing similarities to the coenzyme F420-reducing hydrogenase (YP_004624049) from *Pyrococcus yayanosii* CH1 (YP_002958434) 81%), the coenzyme F420-reducing hydrogenase (YP_002958434) from *Thermococcus gammatolerans* EJ3 (77%), the coenzyme F420-reducing hydrogenase (YP_004762049) from *Thermococcus* sp. 4557 (72%), the coenzyme F420-reducing hydrogenase (YP_001097176) from *Methanococcus maripaludis* (33%) and the coenzyme F420-reducing hydrogenase (NP_987940) from *Methanococcus maripaludis* S2 (33%).

Example 2

Expression of Hydrogenase Gene Under Formate Growth Conditions

It was reported that *T. onnurineus* NA1 can grow using exogenous formate as a substrate and the growth has a close relationship with hydrogen production. It was shown that, when formate was used as the substrate, the mRNA expression levels of 10 ORFs before the fdh2-mfh2-mnh2 cluster were at least 2-fold up-regulated compared to YPS, but the expression levels of ORFs in other hydrogenase gene clusters were relatively constant (mbx, frh and mch) and inhibited (mbh, sulfI and mfh1). Such results suggest that the fdh2-mfh2-mnh2 cluster can react with formate. Because F420-reducing hydrogenase genes are located immediately before the fdh2-mfh2-mnh2 cluster, it was expected that F420-reducing hydrogenase can influence growth and hydrogen production when formate is used as a substrate.

Figure 1B:
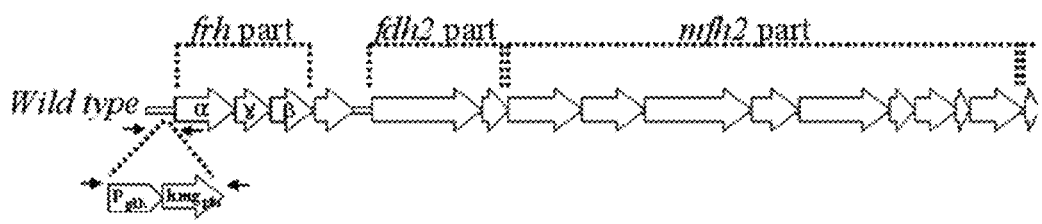
FIG. 1B is a schematic view showing a strategy for construction of a mutant strain. A $P_{gdh}hmg_{Pfu}$ cassette was introduced before the alpha-subunit gene (Ton__1559) of F420-reducing hydrogenase (frh). The locations of the primers used for confirmation are indicated by black arrows below the corresponding genes.
Figure 2:
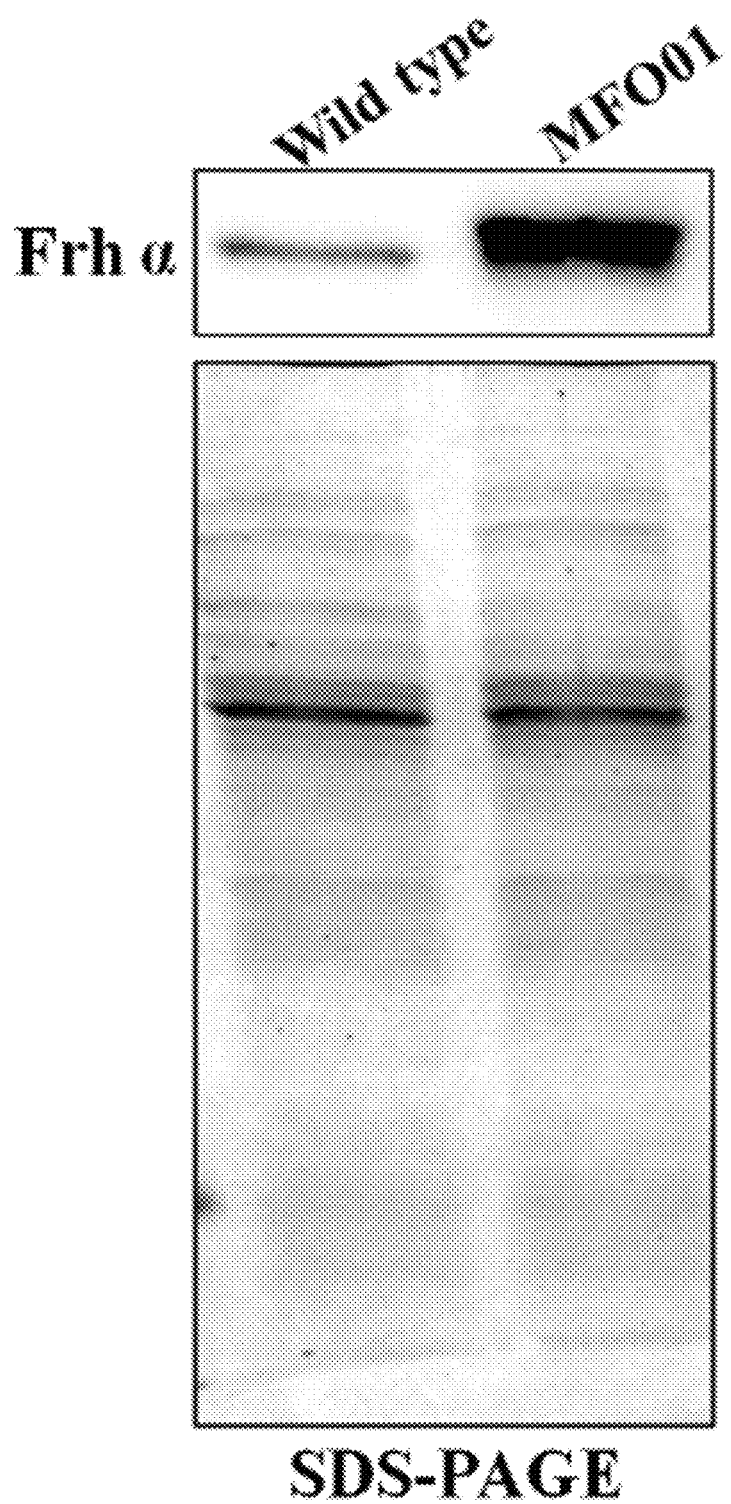
FIG. 2 shows the results of Western blot analysis conducted to measure the protein level of F420-reducing hydrogenase (frh). SDS-PAGE stained with Coomassie brilliant blue R-250 is shown below the Western blot.

In order to over-express F420-reducing hydrogenase, a strong promoter of glutamate dehydrogenase ($P_{gdh}$) *P. furiosus* having HMG-CoA reductase gene was introduced to prepare MFO01 (FIG. 1B). Due to the insertion of the strong promoter, the expression of the F420-reducing hydrogenase gene was successfully increased. When the expression level of the protein was compared between the wild-type strain and the mutant strain, it was shown to be 5 times higher in the mutant strain than in the wild-type strain.

Figure 3A:
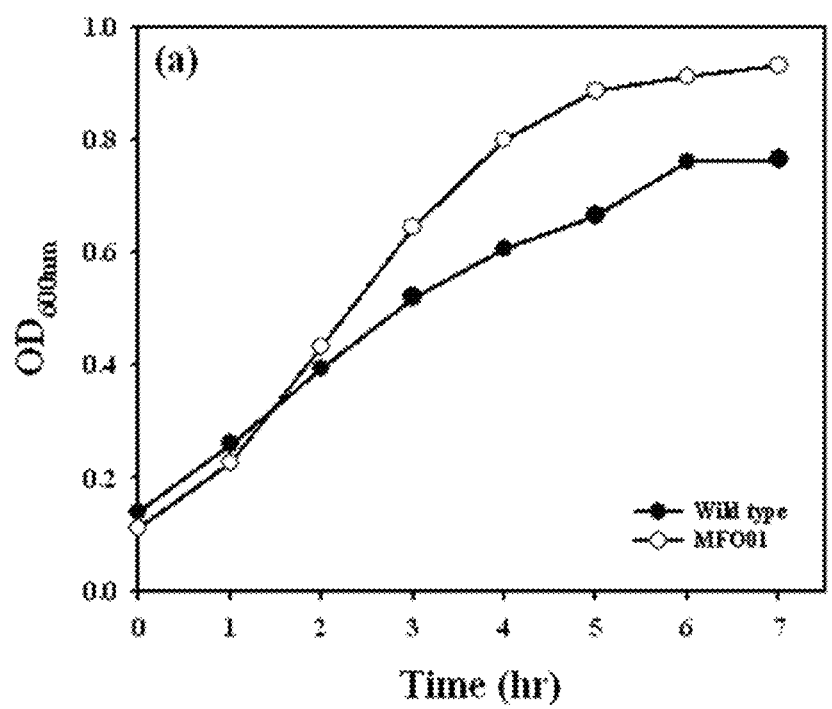
FIGS. 3A and 3B show changes in the production of hydrogen in a wild-type strain and a mutant in CSTR fermentation performed using formate as a substrate.
Figure 3B:
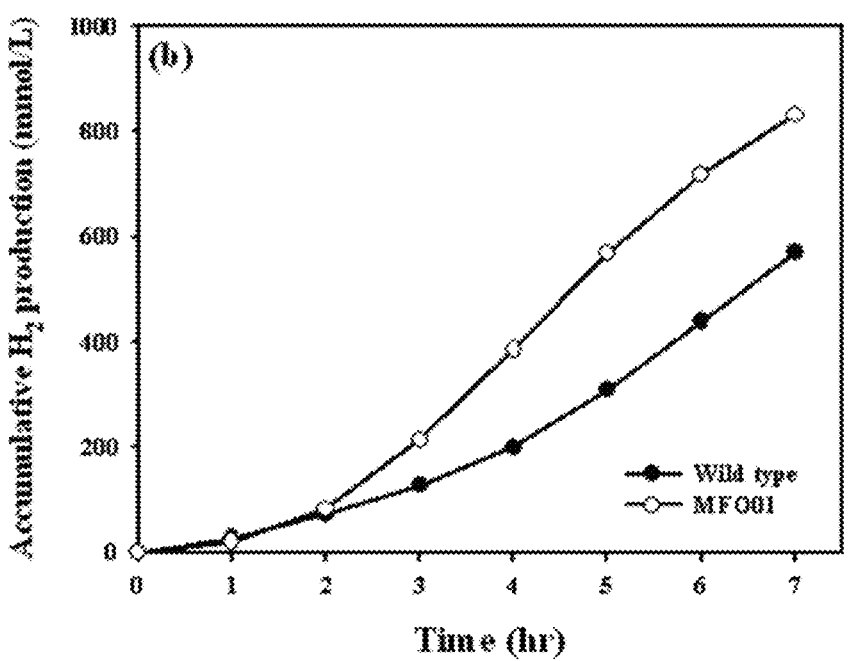
Figure 4:
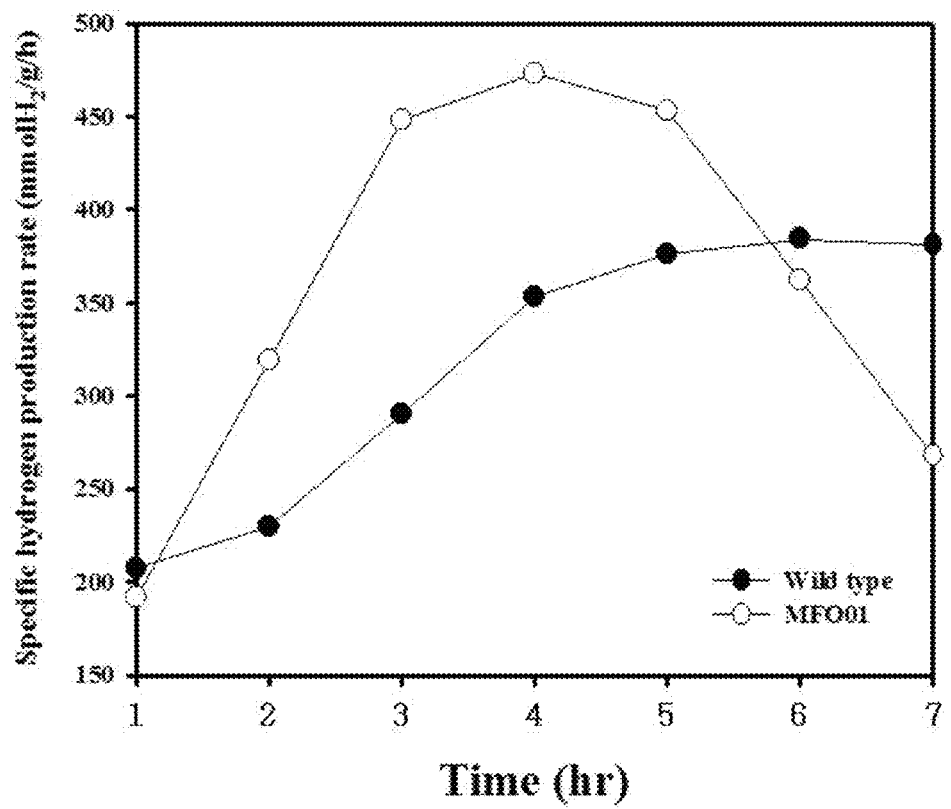
FIG. 4 shows the kinetic analysis of the production of hydrogen in a wild-type strain and a mutant in CSTR fermentation performed using formate as a substrate.

To measure cell growth and hydrogen production in the mutant strain, culture was performed in a CSTR fermenter using formate as a substrate. It could be seen that the mutant strain showed faster growth than the wild-type strain after 2 hours of culture and the doubling time of the mutant strain was 61 minutes, which is significantly shorter than the doubling time (80 minutes) of the wild-type strain (FIG. 3A). Such results indicate that the growth of the cells was promoted by the over-expression of F420-reducing hydrogenase (frh). In addition, it could be seen that the accumulative production of hydrogen was higher in the mutant strain than in the wild-type strain (FIG. 3B). The maximum specific $H_2$ production rate per unit cell was 384 mmol/g/h and 472 mmol/g/h in the mutant strain, and this production of biohydrogen from formate in the mutant strain is the highest value that the present inventors (FIG. 4). In conclusion, the over-expression of F420-reducing hydrogenase in *T. onnurineus* NA1 made it possible to increase cell growth and hydrogen production.

As described above, the mutant strain according to the present invention showed an increase in growth rate of about 31% and a hydrogen production rate per unit time of about 20% compared to a wild-type *Thermococcus* strain. The method of producing hydrogen using the mutant strain according to the present invention has advantages over a conventional chemical production method in that it does not require the conditions of high-temperature and high-pressure, can generate hydrogen under the conditions of room temperature and atmospheric pressure, and does not generate harmful byproducts. In addition, the method of the present invention has advantages in that it can produce high-purity hydrogen with high efficiency and can produce hydrogen even under high-temperature conditions, compared to conventional techniques of producing hydrogen using microorganisms.

What is claimed is:

1. A mutant strain of *Thermococcus* spp., which comprises overexpressed F420-reducing hydrogenase and has an increase ability to produce hydrogen.

2. The mutant strain of claim 1, wherein the *Thermococcus* spp. is *Thermococcus onnurineus*.

3. The mutant strain of claim 1, wherein the *Thermococcus* spp. is a microorganism deposited under accession number KCTC 12356BP.

4. A method for producing hydrogen, comprising:
   mutating *Thermococcus* spp. to increase the expression of F420-reducing hydrogenase therein; and
   culturing the mutated *Thermococcus* spp. in a medium containing formate.

5. The method of claim 4, wherein the *Thermococcus* spp. is *Thermococcus onnurineus*.

6. The method of claim 4, wherein the *Thermococcus* spp. is a microorganism deposited under accession number KCTC 12356BP.

7. The method of claim 4, wherein the increase in the expression of the F420-reducing hydrogenase corresponds to an increase in the copy number of the F420-reducing hydrogenase gene, an increase in the transcription of the gene, an increase in the translation of the gene, an increase in the stability of the F420-reducing hydrogenase, or a combination thereof.

8. The method of claim 7, wherein the increase in the transcription of the F420-hydrogeanse gene is achieved using a strong constitutive promoter operably linked to the gene.

9. The method of claim 8, wherein the promoter is a promoter of glutamate dehydrogenase (Pgdh).

\* \* \* \* \*